United States Patent [19]
Py

[11] Patent Number: 5,133,702
[45] Date of Patent: Jul. 28, 1992

[54] OCULAR TREATMENT APPARATUS

[75] Inventor: Daniel Py, Short Hills, N.J.

[73] Assignee: O.P.T.I.C., Short Hills, N.J.

[21] Appl. No.: 635,300

[22] Filed: Dec. 28, 1990

Related U.S. Application Data

[63] Continuation of Ser. No. 452,782, Dec. 19, 1989, Pat. No. 4,981,479, which is a continuation-in-part of Ser. No. 267,526, Nov. 4, 1988, Pat. No. 4,946,452, which is a continuation-in-part of Ser. No. 118,388, Nov. 6, 1987, Pat. No. 4,792,334.

[51] Int. Cl.$^5$ ............................................. A61H 33/04
[52] U.S. Cl. ..................... 604/302; 604/298; 604/300; 604/301
[58] Field of Search ............... 604/300, 301, 302, 295, 604/298

[56]  References Cited

U.S. PATENT DOCUMENTS

| | | | |
|---|---|---|---|
| 3,279,446 | 10/1966 | Mings | 128/233 |
| 3,439,674 | 4/1969 | Lelicoff | 128/233 |
| 3,934,590 | 1/1976 | Campagna et al. | 604/302 |
| 4,085,750 | 4/1978 | Bosshold | 128/233 |
| 4,131,115 | 12/1978 | Peng | 128/249 |
| 4,386,608 | 6/1983 | Ehrlich | 604/298 |
| 4,531,944 | 7/1985 | Bechtle | 604/302 |
| 4,543,096 | 9/1985 | Keene | 604/300 |
| 4,573,982 | 3/1986 | Forbes et al. | 604/300 |
| 4,605,398 | 8/1986 | Herrick | 604/300 |
| 4,685,906 | 8/1987 | Murphy | 604/300 |
| 4,733,802 | 3/1988 | Sheldon | 222/181 |
| 4,981,479 | 1/1991 | Py | 604/300 |

FOREIGN PATENT DOCUMENTS 0145541 6/1985 European Pat. Off. .
0197344 10/1986 European Pat. Off. .
1025304 4/1953 France .

OTHER PUBLICATIONS

Sheldon, G. M., "Self-Administration of Eyedrops," Opthalmic Surgery, May 1987, pp. 393-394.
Letocha, Charles E., "Methods for Self-Administration of Eyedrops," Ann Ophthalmol, 17:768-769 (1985).

Primary Examiner—Allen M. Ostrager
Attorney, Agent, or Firm—Kenyon & Kenyon

[57]  ABSTRACT

An apparatus for applying medicament to an eye has an inner casing and an outer casing coupled to the inner casing and moveable relative thereto. An eyecup is supported on one end of the inner casing. The eyecup defines a surface shaped to conformably engage the facial tissue surrounding an eye. An ocular vial supported with the inner casing. The ocular vial holds medicament for release into an eye. An eyelid displacing member is coupled to the outer casing and slideably mounted through the inner casing. The eyelid displacing member includes a depresser tab adapted to engage the facial tissue below an eye. The depresser tab engages the facial tissue upon moving the outer casing toward the inner casing, thus displacing the lower eyelid to expose the ocular cul-de-sac. A dispensing member is supported by the outer casing. The dispensing member is adapted to actuate the ocular vial upon moving the outer casing toward the inner casing, to release medicament onto the exposed ocular cul-de-sac of the eye.

5 Claims, 13 Drawing Sheets

OCULAR TREATMENT APPARATUS

This application is a continuation of U.S. application Ser. No. 07/452,782, Dec. 19, 1989, now U.S. Pat. No. 4,981,479, copending herewith, which is a continuation-in-part of U.S. application Ser. No. 07/267,526, filed Nov. 4, 1988, now U.S. Pat. No. 4,946,452, which is in turn a continuation-in-part of U.S. application Ser. No. 7/118,388 filed Nov. 6, 1987, now U.S. Pat. No. 4,792,334.

FIELD OF THE INVENTION

The present invention is directed to ocular treatment apparatus and, in particular, to ocular treatment apparatus that can apply eye drops of liquid medicament safely and easily.

BACKGROUND INFORMATION

Most people encounter difficulty in applying drops to their eyes. Because the eye is very sensitive, most individuals find it difficult to control reflexive blinking when applying drops thereto. Also, eye drop users often have poor vision. Poor vision makes it difficult to position the tip of the dropper bottle over the eye and frequently causes drops to be incorrectly applied to the nose or cheek. Moreover, elderly people often have difficulty holding a dropper bottle steady or encounter difficulty in squeezing the bottle to apply a proper quantity of medicament to the eye.

Even if the liquid medicament is properly applied to the cornea, the medicament's effectiveness is limited. The maximum volume of a drop of liquid medicament which can be introduced into contact with an eye at one time is about 30 microliters. Any amount that is greater usually spills over the eyelid onto the cheek. When eye drops are applied to the surface of the eyeball, blinking and natural tear flow combine to limit the time to a few minutes that liquid medicament will remain effective. However, if medicament is applied to the cul-de-sac of the conjunctiva, the medicament will remain effective for a longer period of time, maximizing the benefits of applying drops of liquid medicament to the eye.

U.S. Pat. No. 4,543,096 describes and illustrates an apparatus having finger-like projections which are attached to the front of an eye drop bottle to spread the eyelids apart during the eye drop dispensing process. One moveable finger is connected to a lever for depressing the lever and simultaneously causing the eyelids to spread apart while forcing a drop from the dropper bottle. However, the apparatus described in U.S. Pat. No. 4,543,096 will not properly steady the eyeball nor expose the cul-de-sac. Further, the finger-like projections could cause injury to the eye if a user accidentally contacts his cornea with one of the projections. Similarly, U.S. Pat. No. 4,531,944 depicts an apparatus for steadying the tip of a dropper over the eye and further includes a sighting hole to distract the eye. However, this apparatus does not have means to expose the cul-de-sac nor keep the lower eyelid depressed.

Accordingly, an ocular treatment apparatus that is capable of simultaneously steadying the eyeball, orienting the application of the medicament, applying the medicament and exposing the cul-de-sac is desired.

SUMMARY OF THE INVENTION

Generally speaking, in accordance with the invention, an ocular treatment apparatus is provided for applying liquid medicament from a reservoir. The apparatus includes a tubular housing with a first open end adapted to conform to the shape of the facial area surrounding the eye socket. The housing is constructed and arranged to receive, hold and position a reservoir containing the liquid medicament. A sighting opening is included on the housing to properly orient the eye and distract the user from the drops of liquid medicament to be introduced into the eye. An eyelid displacement mechanism is supported on the first open end of the housing at a position diametrically opposed to the sighting opening. The displacement mechanism is adapted to evert the lower eyelid and expose the cul-de-sac.

This combination of an eye focused at the sighting hole and an everted lower eyelid exposes the cul-de-sac so that drops of medicament dispensed into the eye will more easily and directly be applied at or near the cul-de-sac where it is temporarily retained to increase the length of time the medicament will medicate the eyeball. In a further embodiment of the instant invention, the lower eyelid displacement mechanism will simultaneously cause drops to be emitted from the reservoir into the cul-de-sac as the lower eyelid is everted to facilitate application of the drops of liquid medicament. The cul-de-sac is a low sensitivity area as opposed to the cornea area. Therefore application of medicament to the cul-de-sac is more comfortable.

In another embodiment of the invention an ocular treatment apparatus for applying solid or liquid medicament into an eye comprises an inner housing member including an eyepiece portion on a free end thereof. The eyepiece portion defines an opening therein having a peripheral edge shaped for conformable engagement with the facial tissue surrounding an eye. The inner housing member further includes a body portion for receiving a vial of liquid medicament for application to the eye.

An outer housing member of the apparatus has an open free end slideably engaged over the end of the inner housing member opposite the eyepiece portion. The outer housing member defines a medicament displacement member projecting outwardly from its end opposite the free end and projecting into the body portion of the inner housing member. The displacement member is depressible against a flexible vial contained within the body portion of the inner housing member by sliding the outer housing member toward the eyepiece portion for displacing medicament from the vial and, in turn, through the opening in the eyepiece portion and into the eye.

The apparatus further includes means for displacing the lower eyelid of an eye to evert the lower eyelid so that medicament released from the vial is applied to the ocular cul-de-sac of the eye. The means for displacing the lower eyelid preferably include a cushion member having a substantially curved configuration. The cushion member is disposed around the peripheral edge of the eyepiece portion so that the free end of the cushion member is placed between the interior surface of the eyepiece portion and facial tissue of the person. The other end of the cushion member is connected to a flexible bar which, in turn, is connected on its other end to the outer housing member. The flexible bar member presses the cushion member downwardly to evert the lower eyelid when the outer housing member is moved over the inner housing member toward the eyepiece portion for application of medicament into the ocular cul-de-sac.

The present invention is also directed to an apparatus for applying medicament to an eye comprising an inner casing adapted to receive medicament. The inner casing defines a first surface shaped to engage the facial tissue surrounding an eye. The inner casing further defines a first aperture extending therethrough. Medicament is released through the first aperture into an eye. An outer casing of the apparatus is coupled to the inner casing and movable relative thereto.

The apparatus further comprises means for displacing the lower eyelid of an eye to expose the ocular cul-de-sac. The means for displacing is coupled to the outer casing. The apparatus further comprises means for dispensing medicament received within the outer casing onto the exposed ocular cul-de-sac of the eye. The means for dispensing is coupled to the outer casing.

In one embodiment of the present invention, the inner casing includes an eyecup supported on one end thereof, which defines the first surface. The means for displacing includes a displacing member coupled to the outer casing. The displacing member defines a second surface adapted to engage the facial tissue below an eye. The second surface is engageable with facial tissue by moving the outer casing relative to the inner casing, to displace the facial tissue and thus displace the lower eyelid.

The inner casing defines at least one second aperture extending therethrough. The second aperture is adapted to receive the displacing member therethrough. The inner casing further defines at least one guide surface adapted to guide the displacing member toward the facial tissue below an eye.

The apparatus further comprises a vial supported within the inner casing. The vial is adapted to hold medicament and to release medicament in response to the means for dispensing, upon moving the outer casing relative to the inner casing. The means for dispensing includes at least one finger member supported on the outer casing. The finger member is adapted to engage the ocular vial upon moving the outer casing relative to the inner casing to release medicament therefrom.

The apparatus of the present invention further comprises a coil spring seated between the outer casing and the ocular vial. The coil spring thus spring loads the outer casing relative to the inner casing. Preferably, the inner casing defines two second apertures extending therethrough and two guide surfaces. The displacing member defines a first leg and a second leg, and a depresser tab supported therefrom. The depresser tab defines the second surface adapted to engage the facial tissue below an eye. The first and second legs are each received within the two second apertures, respectively. Each leg is in turn coupled on one end to the outer casing.

The depresser tab is engageable with the facial tissue below an eye by moving the outer casing relative to the inner casing, thus moving the depresser legs through the second apertures. The two guide surfaces in turn guide the first and second legs and thus the depresser tab downwardly toward the facial tissue below the eye.

The present invention is directed to yet another apparatus for applying medicament to an eye. The apparatus comprises a first housing member including an eyepiece on one end thereof. The eyepiece defines a first surface shaped to engage the facial tissue adjacent to an eye. The apparatus further comprises an ocular vial adapted to receive medicament supported within the first housing member to release medicament into an eye. A second housing member is coupled to the first housing member and movable relative thereto. The second housing member includes a dispensing member supported therefrom. The dispensing member is adapted to engage the ocular vial by moving the second housing member toward the first housing member to release medicament into an eye.

The apparatus further comprises an eyelid depresser coupled to the second housing member and slideably mounted relative to the first housing member. The eyelid depresser defines a second surface adapted to engage the facial tissue below an eye upon moving the second housing member toward the first housing member. The displaced facial tissue in turn displaces the lower eyelid, to release medicament into the eye.

By employing the apparatus of the present invention, medicament can be applied safely and effectively to an eye. The user simply has to place the apparatus over the eye, so that the eyepiece is seated on the facial tissue around the eye. Once the eyepiece is seated, the apparatus can be easily positioned to release medicament into the eye. There is no need for the user to steady the device over the eye, as with many prior art devices.

The apparatus of the present invention displaces the lower eyelid so as to expose the ocular cul-de-sac. Thus, the problems encountered with reflexive blinking when applying drops to an eye are avoided with the apparatus of the present invention. Moreover, because the apparatus of the present invention exposes the ocular cul-de-sac, the medicament can be applied directly to the cul-de-sac, thus maximizing its effectiveness and comfort to the patient.

Other advantages of the apparatus of the present invention will become apparent in view of the following detailed description and drawings taken in connection therewith.

DETAILED DESCRIPTION

Figure 1:
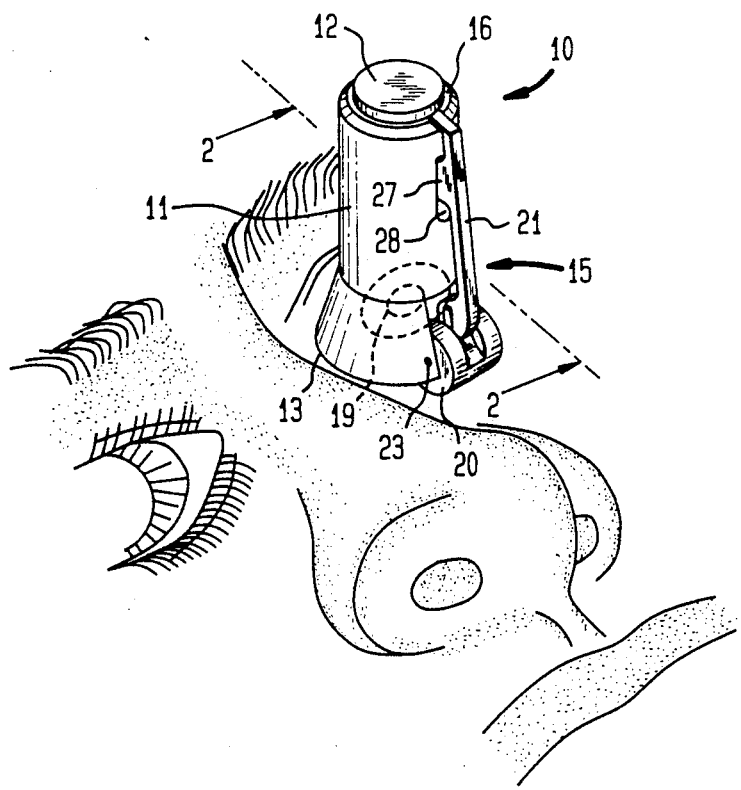
FIG. 1 is a perspective view of a preferred embodiment of the ocular treatment apparatus.
Figure 2:
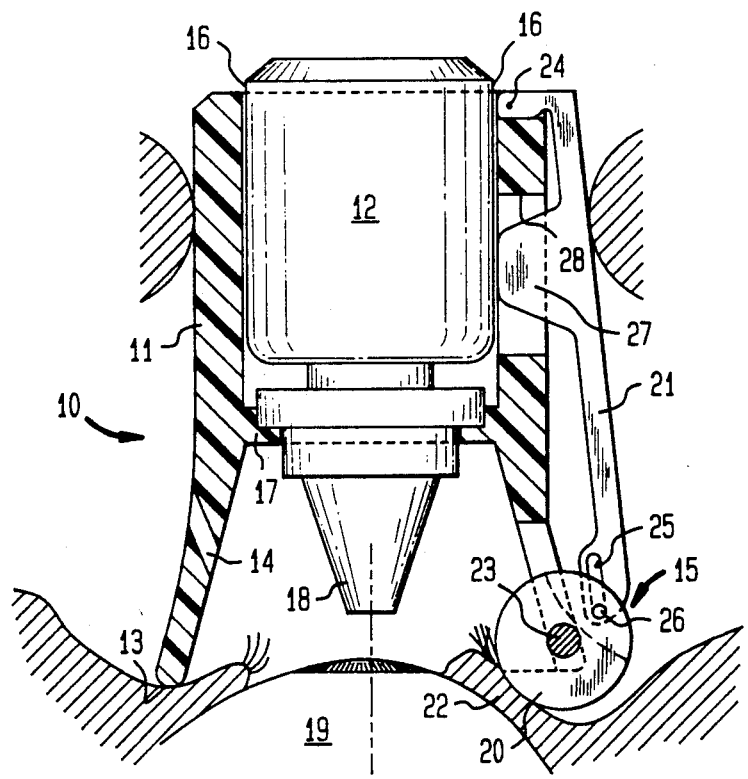
FIG. 2 is a sectional view taken along line 2—2 of FIG. 1.
Figure 3:
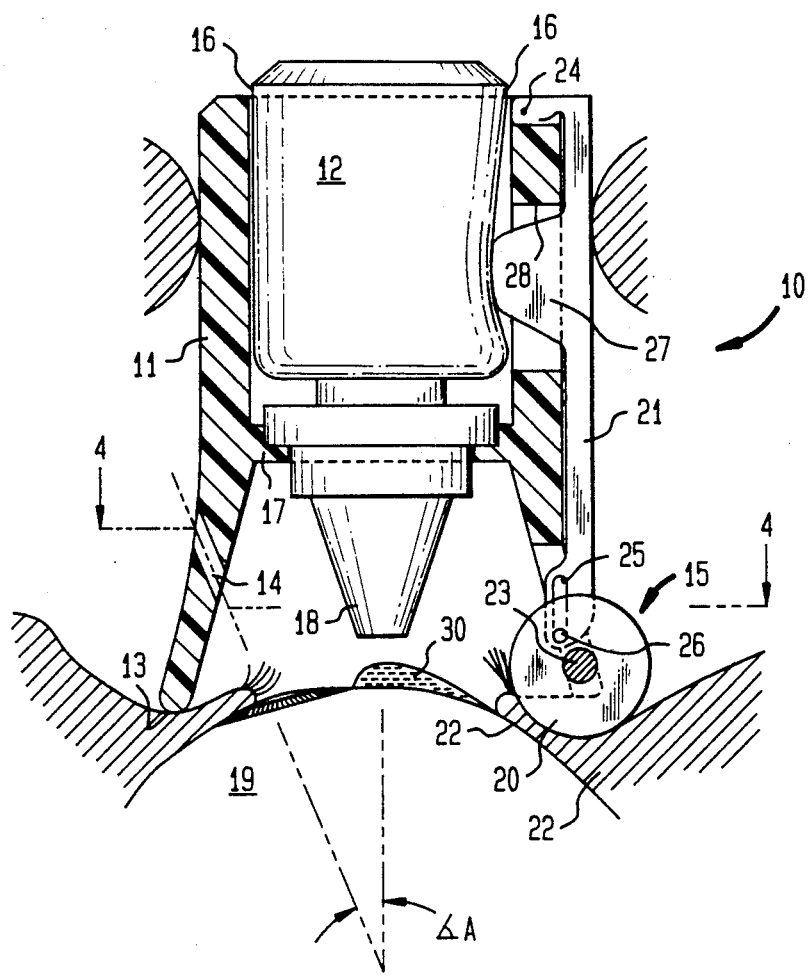
FIG. 3 is a sectional view taken along line 2—2 of FIG. 1 illustrating the operation of the ocular treatment apparatus.
Figure 4:
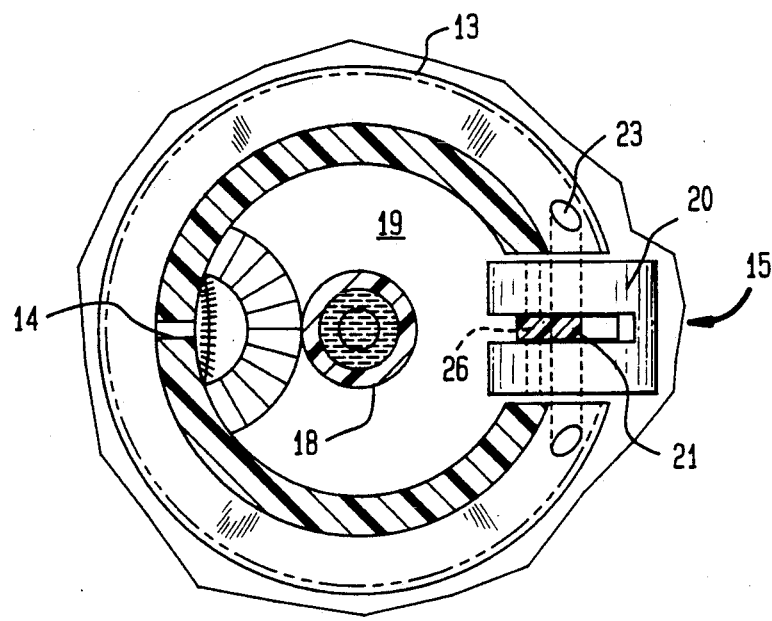
FIG. 4 is a sectional view taken along line 4—4 of FIG. 3.

Referring generally to FIGS. 1 to 4, a preferred embodiment of the ocular treatment apparatus of the instant invention is indicated generally at 10. Apparatus 10 includes a tubular housing 11 constructed and arranged to receive and hold a dropper bottle 12. Housing 11 includes a front opening 13 which conforms to the facial area surrounding an eye 19. A sighting opening 14 is positioned in the tubular housing proximate to front opening 13 to properly orient an eyeball during use of the ocular treatment apparatus. A displacement mechanism, illustrated generally at 15, is included on housing 11 at a position generally diametrically opposite sighting opening 14. Displacement mechanism 15 retracts the lower eyelid to expose a surface of the eye below the pupil for application of medicament from reservoir 12.

In an exemplary embodiment, housing 11 is constructed and arranged to retain a dropper bottle 12. However, the housing can be modified to hold a dropper, single dose dropper vial, pressurized propellant device, or any other suitable applicator that stores and can deliver liquid medicament to the eye.

Accordingly, housing 11 includes a rear opening 16 shaped to receive dropper bottle 12. Housing 11 includes a radially disposed collar 17 for receiving and releasably securing the neck of dropper bottle 12. Housing 11 is configured so that the longitudinal axis of dropper bottle 12 is substantially parallel to and substantially aligned with the longitudinal axis of housing 11.

Front opening 13 is configured to nest in the facial area surrounding the eye socket. It is shaped so that apparatus 10 may be placed over the eye and easily maintained in a steady position with the tip of a dropper bottle nozzle 18 correctly positioned over eye 19. In this manner, when front opening 13 is positioned to surround the eye and a person tilts his head back, the drop of medicament falling from nozzle 18 will fall into the eye 19 by gravity.

An eyelid displacement mechanism, located generally at 15, for safely and comfortably retracting the lower eyelid is included in the ocular treatment apparatus. It is desirable for the medicament to flow to the interior cul-de-sac to increase the effectiveness of the medicament. Sliding the lower eyelid back and down helps to uncover the ocular cul-de-sac which is a nonsensitive part of the conjunctiva. Displacement mechanism 15 includes an engagement body 20 and drive member 21. Engagement body 20 is a curved member which contacts lower eyelid 22 when front opening 13 is positioned around the eye. Engagement body 20 is rotatably mounted to housing 11 at front opening 13 by axle 23. When curved engagement body 20 is caused to partially rotate, it everts lower eyelid 22 and exposes the cul-de-sac.

The curved design of engagement body 20 provides several important benefits. The area of contact between the curved surface of engagement body 20 and lower eyelid 22 is considerable. This helps evert the eyelid properly and feels similar to using one's own finger to evert the eyelid. The wide engagement surface also makes exact placement of the engagement body 20 less critical. The curved surface of engagement body 20 also prevents injuries which can occur when an instrument for sliding the eyelids back is utilized.

To utilize apparatus 10, front opening end 13 is placed over the eye with engagement body 20 resting against lower eyelid 22. As depicted generally in FIG. 3, an elongated drive shaft 21 is then displaced to partially rotate engagement body 20. A first end of drive shaft 21 is pivotally connected to housing 11 by pivot pin 24. A second end of drive shaft 21 is pivotally and slideably connected to engagement body 20 at slot 25, which is positioned around drive pin 26. Drive shaft 21 includes a projection 27 intermediate its first and second ends. Housing 11 defines a housing slot 28 through rear opening 16 aligned with projection 27 so that when drive shaft 21 is moved towards housing 11, projection 27 will pass through housing slot 28 to compress dropper bottle 12 and force drops 30 of liquid medicament from nozzle 18. As drive shaft 21 moves towards housing 11, the sides of slot 25 push against drive pin 26 to partially rotate engagement body 20 to retract lower eyelid 22 coincident with liquid 30 being introduced to the eye from nozzle 18.

Sighting opening 14 is positioned proximate front open end 13 to correctly orient the eye and help uncover the cul-de-sac. It also helps control reflexive blinking which is often caused by the user sensing something approaching his exposed eye. Sighting opening 14 is provided in housing 11 near front opening 13 at a position diametrically opposed to curved engagement body 20, so that a user will have his eye steadied in an upwardly rotated position when his lower eyelid is everted. To properly uncover the cul-de-sac, sighting opening 14 should be positioned near front opening 13 so that the eye will be oriented upwardly though an angle A which should be at least 30°. However, in a preferred embodiment angle A is greater than 35°. Because the only light perceived by the user passes through sighting hole 14, a person having poor vision is assisted in properly orienting their eyeball.

Figure 5:
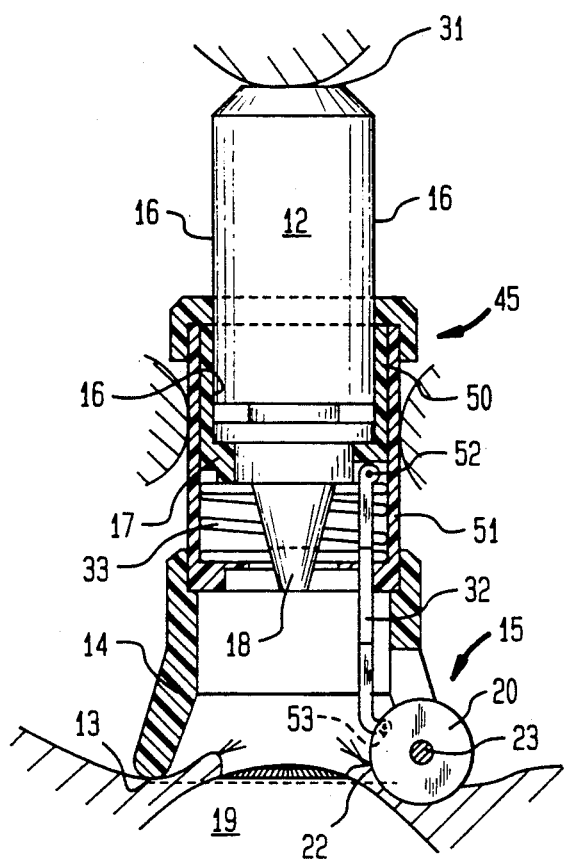
FIG. 5 is a sectional view of an alternative embodiment of the ocular treatment apparatus.
Figure 6:
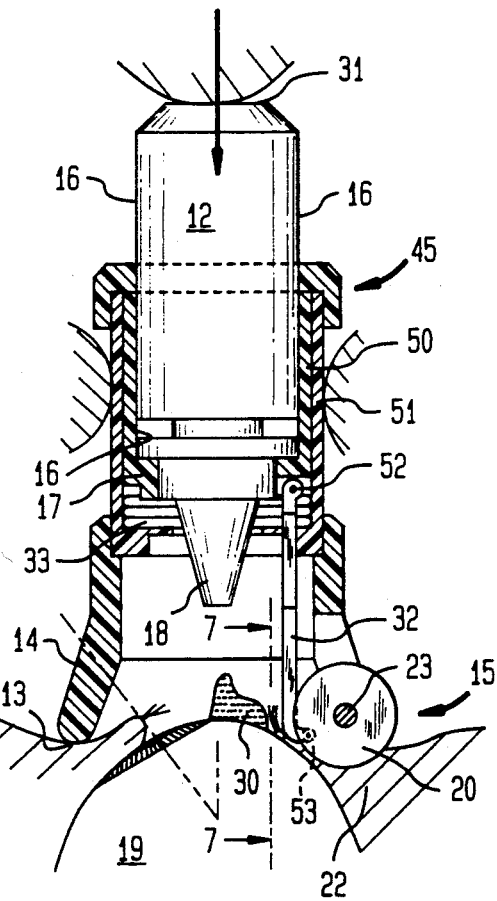
FIG. 6 is a sectional view illustrating the operation of the apparatus shown in FIG. 5.
Figure 7:
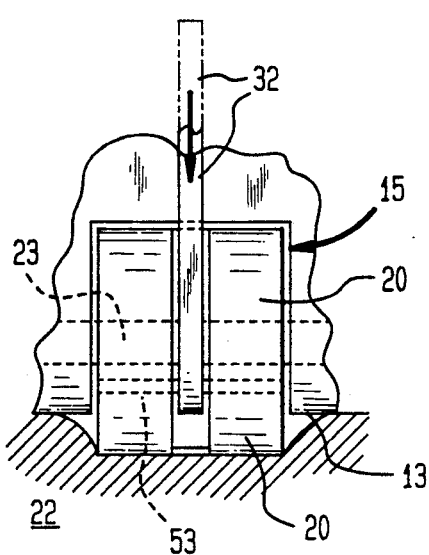
FIG. 7 is a sectional view taken along line 7—7 of FIG. 6.

Referring next to FIGS. 5 through 7, a further embodiment of the ocular treatment apparatus, generally indicated as 45 is depicted, like reference numerals being utilized to depict like elements discussed above. This embodiment has the same curved engagement body 20, front opening 13, sighting hole 14 and collar 17.

However, the mechanism for rotating engagement body 20 is structurally distinct. Bottle 12 rests in slidable seat 50. Seat 50 can slide within outside tubular housing 51 and is upwardly biased by spring 33. Vertical drive shaft 32 has two ends. Its first end is pivotally connected to slideable seat 50 by pin 52. The second end of vertical drive member 32 is slideably and pivotally connected to curved engagement body 20, by drive pin 53. When bottle 12 is inserted into the housing to compress spring 33, vertical drive shaft 32 causes curved engagement body 20 to partially rotate, everting lower eyelid 22.

Specifically, a user places front opening 13 of apparatus 45 over the eye and contacts the lower eyelid with engagement body 20. To dispense drops of liquid medicament, the user again peers through sighting opening 14. To evert the lower eyelid, end 31 of dropper bottle 12 is pushed into the housing, causing vertical drive member 32 to rotate curved engagement body 20.

Accordingly, this further embodiment causes the force necessary to evert the lower eyelid to be applied in a direction which will increase the contacting pressure between engagement body 20 and lower eyelid 22. This will decrease the chance of slippage to insure that lower eyelid 22 is everted. Spring 33 returns the apparatus to its original position shown in FIG. 5.

Accordingly, when the ocular treatment apparatus of the instant invention is used to apply liquid medicament to the eye, the above indicated advantages are observed. The dropper bottle is steadied over the eye in a correct orientation; the cul-de-sac of the conjunctiva is exposed by the combination of orienting the eyeball in an upwardly gazing position while everting the lower eyelid; involuntary blinking is prevented by the user focusing on light passing through the sighting opening at the same time that the lower eyelid is held in a depressed position. Therefore, drops of liquid medicament can be applied to the eye so that the medicament will flow to the cul-de-sac to increase the half life of its effectiveness.

Turning to FIGS. 8 through 11 another embodiment of the ocular treatment apparatus of the invention is illustrated generally as 110. The apparatus 110 includes an inner housing 112 slideably engaged within an outer housing 114. The inner housing 112 includes an eyepiece portion 120 and a substantially cylindrical portion 116 having an open end 118. The peripheral edge of the eyepiece portion 120 defines an open end 122 shaped to conform to the contour of the facial tissue surrounding the eye.

The eyepiece portion 120 has defined in an upper wall thereof a sighting opening 124. The sighting opening 124 is located near the open end 122 of the eyepiece and operates to help correctly orient the eye for uncovering the cul-de-sac in the same manner as the sighting opening 14 described above in relation to the previous embodiments. Sighting opening 124, therefore, is similarly positioned so that the eye will be oriented upwardly through an angle A which is at least 30°. When the eyepiece 120 is placed against the facial tissue around the eye, the shape of the peripheral edge of the eyepiece prevents light from passing between the eyepiece and facial tissue. Substantially all of the light entering the eye thus enters through the sighting opening 124.

The inner housing 112 of apparatus 110 defines an elongated channel 128 in an outer wall thereof extending in the axial direction of the apparatus. The end of channel 128 near the open end 118 of inner housing 112 is shaped to form a seat 130 recessed in the channel 128 for a ball 132. The ball 132 is preferably made of metal, such as steel. When the apparatus 110 is rotated and aligned over the eye, the ball 132 rolls from the recessed seat 130 and into the channel 128. In this manner, the ball 132 rolls down the channel 128 and hits the bottom wall thereof. The action of the ball striking the bottom wall of the channel transmits vibrations through the wall of the apparatus 110 and into the facial tissue and bone structure of the person. In this way the person can feel or hear the falling ball and thus know when the apparatus is properly aligned over the eye. This is especially useful for persons that have poor eyesight or are deaf, since they can simply feel the vibrations of the rolling ball.

The apparatus 110 further includes a substantially cylindrical shaped vial 134 for containing liquid medicament. The vial 134 is shaped to slideably fit within the cylindrical portion 116 of inner housing 112. The vial includes a body 136 for holding liquid medicament, a neck 138, and a nozzle 140 for releasing drops of liquid. The body 136 of the vial is attached to the inner housing 116 in a known manner, such as by forming a snap fit. Similarly, the body 116 may be molded as a single piece with the inner housing 116. The shape of the nozzle 140 is known, and may be the same as the nozzle 18 described above in relation to the previous embodiments. The body 136 of the vial defines a cavity 142 therein coaxial with the apparatus 110 and extending along a substantial portion of the body 136. As can be seen, the closed end of cavity 142 is located near the opening of neck 138. The vial 138 is formed of a flexible plastic material, and, as will be hereinafter described, the closed end of cavity 142 is pressed forward in order to release medicament into the eye.

The outer housing 114 of apparatus 110 is slideably engaged over inner housing 112 through an open end 144. Outer housing 114 further defines a closed end 146 and a displacement member 148 projecting outwardly from closed end 146 and coaxial with the apparatus 110. A first lobe 150 is formed in the outer wall of inner housing 112, and a second lobe 152 is formed on the inner wall of outer housing 114 below first lobe 150, to prevent outer housing 114 and inner housing 112 from sliding apart. As can be seen, by pressing outer housing 114 toward eyepiece 120, the displacement member 148 forces the closed end of cavity 142 forward in order to displace medicament into the eye. Third lobes 154, 154 are preferably formed on the outer wall of inner housing 112 below first lobe 150, and second lobe 152, to limit the downward stroke of outer housing 114, and thus permit only a predetermined volume of medicament to be displaced through nozzle 140.

Figure 8:
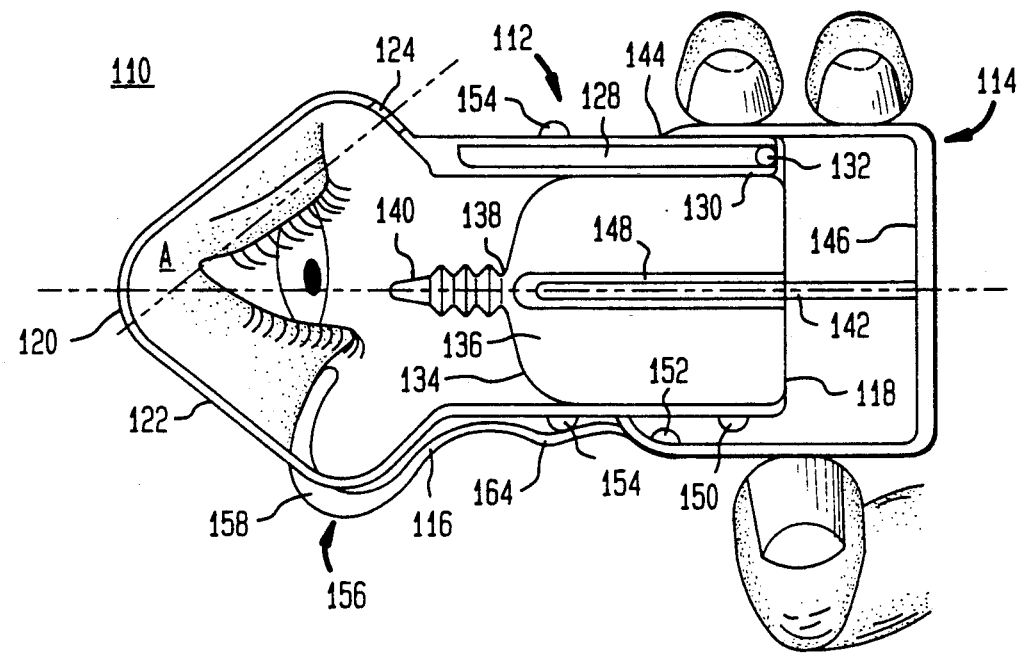
FIG. 8 is a side plan view in partial cross-section of another ocular treatment apparatus embodying the invention shown placed over an eye.
Figure 9:
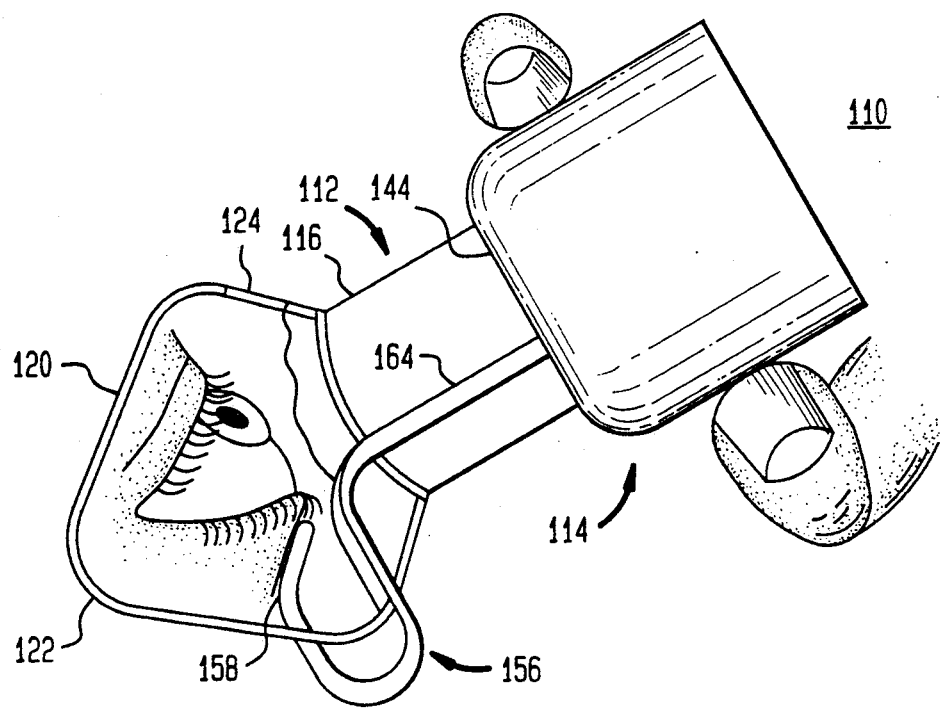
FIG. 9 is a side plan view of the apparatus of FIG. 8 shown aligned over an eye and illustrating a partial cross-sectional view of the eyepiece portion.
Figure 10:
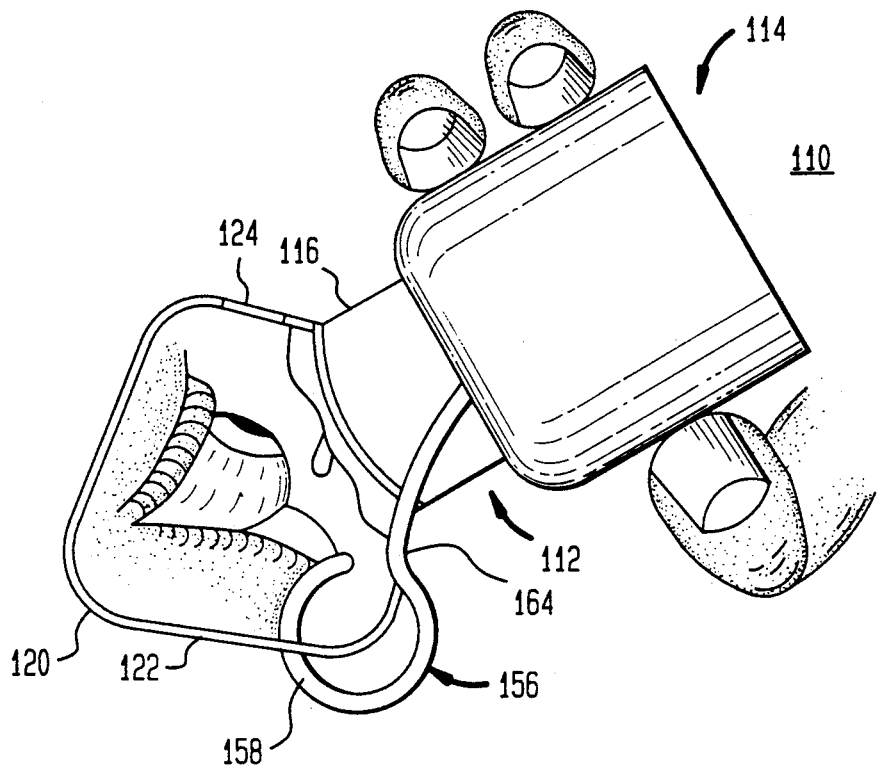
FIG. 10 is a side plan view of the apparatus of FIG. 8 shown applying a drop of liquid medicament into an eye and also illustrating a partial cross-sectional view of the eyepiece portion.
Figure 11:
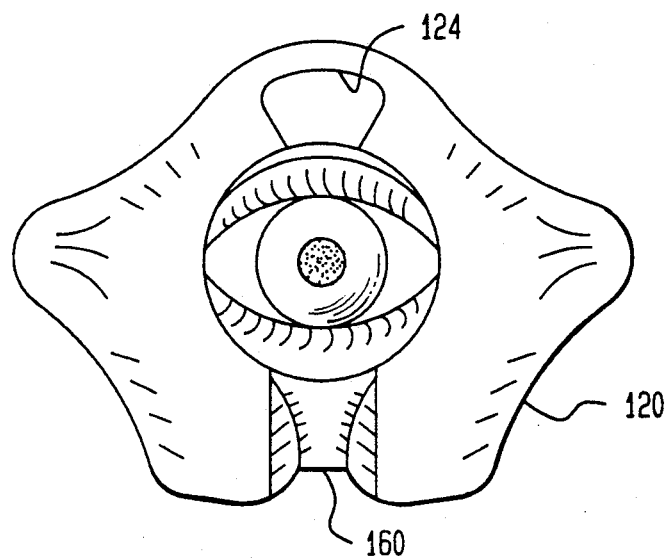
FIG. 11 is a front plan view illustrating the eyepiece portion of the apparatus of FIG. 8.

The apparatus 110 further includes a cushion member 156 formed of a flexible polymeric material. The cushion member 156 includes on its free end a pad 158 having a generally curved shape to fit around the edge of eyepiece 120 and rest between the inner surface of eyepiece 120 and the facial tissue of the person, as best shown in FIGS. 8 through 10. Turning to FIG. 11, eyepiece 120 further defines an indentation 160 formed in a surface thereof and extending radially through the peripheral edge in an area diametrically opposed to sighting opening 124. As can be seen, the free end of pad 158 is slideably fitted around the edge of eyepiece 120 and through indentation 160. The other end of pad 158 is connected to one end of a flexible plastic bar 164 of the cushion member which, in turn, is connected on its other end to the edge of open end 144 of outer housing 114. The bar 164 of the cushion member is attached to outer housing 114 in a known manner, such as ultrasonic welding.

The cushion member 156 is provided for safely and comfortably retracting downwardly the lower eyelid to permit medicament to flow to the interior cul-de-sac, and thus increase the comfort to the person and effectiveness of treatment. The free end of pad 158 contacts the lower eyelid 22 when eyepiece 120 is positioned over the eye. When the outer housing 114 is pressed toward the eyepiece 120, the flexible bar 160 presses the pad 158 against the indentation 160, and thus gently presses the pad downwardly to evert the lower eyelid 22 and expose the cul-de-sac, as illustrated in FIGS. 9 and 10. When the pressure is released from the outer housing, the flexible bar 164 pushes outer housing 114 back toward its initial position and away from inner housing 112.

To utilize apparatus 110, eyepiece 120 is placed over the eye so that it is conformably engaged with the facial tissue surrounding the eye, as shown in FIG. 8. The user then looks through sighting opening 124 to properly orient the eye and tilts his or her head back so that the apparatus 110 is rotated toward a vertical position, as shown in FIG. 9. The user knows that the apparatus has been rotated far enough when the ball 132 is displaced from its seat 130 and hits the bottom wall of channel 128. The user then presses the outer housing 114 toward the eyepiece 120.

The displacement member 148, in turn, simultaneously forces the closed end of cavity 142 toward nozzle 140 and displaces a predetermined volume of medicament through nozzle 140 and into the eye, as shown in FIG. 10. The downward stroke of outer housing 114 simultaneously causes the plastic bar 162 to press pad 158 against the indentation 160, and thus gently press the pad downwardly to evert the lower eyelid 22 and expose the cul-de-sac to receive the liquid or solid medicament.

It should be noted that changes can be made in the above constructions without departing from the spirit and scope of the present invention. For example, the medicament vial 134 of the apparatus 110 can be an aerosol container that releases medicament under pressure and without the need for displacement member 148.

Figure 12:
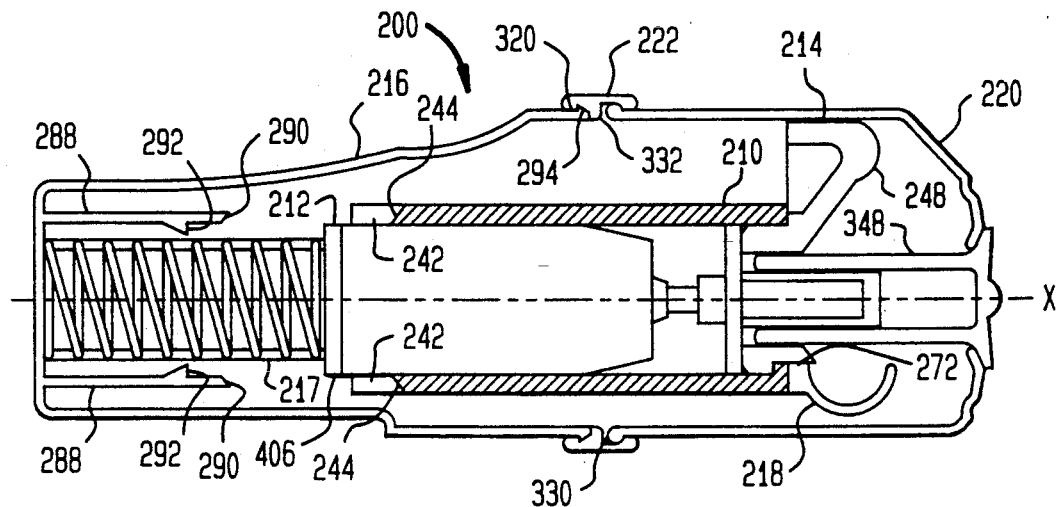
FIG. 12 is a partial cross-sectional view of another ocular treatment apparatus embodying the present invention.
Figure 13:
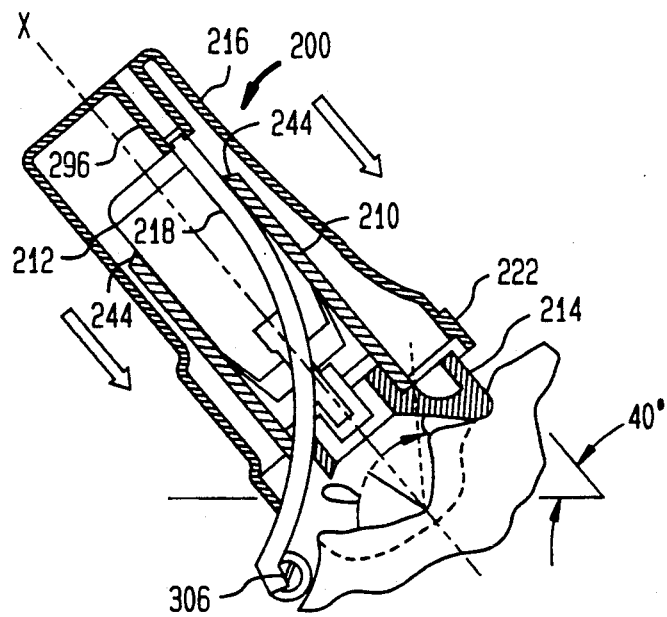
FIG. 13 is another partial cross-sectional view of the apparatus of FIG. 12, illustrating the operation of the apparatus in applying medicament to an eye.

In FIGS. 12 and 13, another ocular treatment apparatus embodying the present invention is indicated generally by the reference numeral 200. The apparatus 200 comprises an inner casing 210, an ocular vial 212 (illustrated schematically) mounted within the inner casing 210, and an eyecup 214 mounted to one end of the inner casing 210. The apparatus 200 further comprises an outer casing 216 mounted over the inner casing 210, and an eyelid depresser 218 coupled to the outer casing 216 and slideably mounted within the inner casing 210.

A tamper-resistant ring 222 is coupled to one end of the outer casing 216, and a coil spring 217 is mounted between the outer casing 216 and the ocular vial 212. A cover 220 is removeably mounted over the eyecup 214, and coupled to the tamper-resistant ring 222, to cover the end of the apparatus 200. The various components of the apparatus 200 are preferably made of polymeric materials suitable for pharmaceutical uses.

As shown in FIG. 13, the apparatus 200 is used to release medicament from the vial 212 onto the exposed ocular cul-de-sac of an eye. The eyecup 214 is placed over the facial tissue surrounding the eye, and the outer casing 216 is moved toward the inner casing 210, as indicated by the arrows in FIG. 13. The movement of the outer casing 216 in turn pushes the eyelid depresser 218 downwardly. The eyelid depresser 218 then gently engages the facial tissue below the eye, and thus displaces the lower eyelid so as to expose the ocular cul-de-sac. The movement of the outer casing 216 also actuates the ocular vial 212 to release a drop of medicament once the ocular cul-de-sac is exposed.

Turning to FIGS. 14 through 17, the inner casing 210 is shown in further detail. The inner casing 210 defines a top wall 224, a bottom end 225, and an aperture 226 extending therethrough. The aperture 226 is concentric with the longitudinal axis X of the inner casing 210, and is defined by a substantially cylindrical wall 228 extending between the top wall 224 and bottom end 225. Four indentations 230 are formed within the cylindrical wall 228. The indentations 230 are equally spaced apart from each other, and each projects radially outward from the X axis and extends along the axial length of the cylindrical wall 228. The cylindrical wall 228 is dimensioned to receive the ocular vial 212, and the indentations 230 are adapted to position the ocular vial in place.

Figure 15:
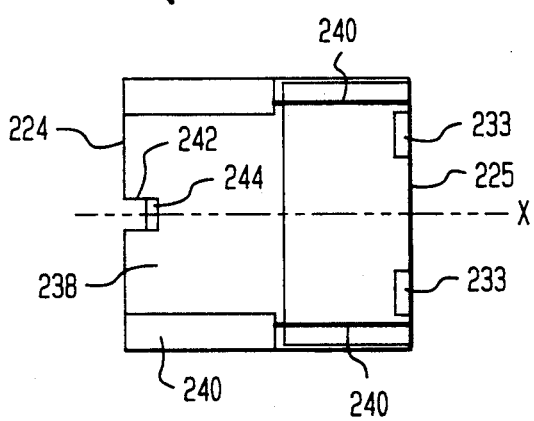
FIG. 15 is a top plan view of the inner casing of FIG. 14.

The inner casing 210 further defines two rectangular apertures 232, each extending through the top wall 224, and two indentations 233 extending into the edge of the bottom end 225, as shown in FIG. 15. The apertures 232 and indentations 233 are dimensioned to permit the eyelid depresser 218 to slide therethrough, as will be described further below.

Figure 14:
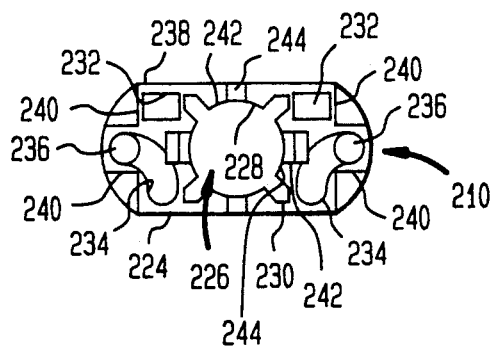
FIG. 14 is a top end plan view of the inner casing of the apparatus of FIG. 12.

The inner casing 210 further defines two channels 234 extending therethrough between the top wall 224 and the bottom end 225. As shown in FIG. 14, each channel 234 spirals inwardly from the top wall 224 substantially toward the axial center of the casing 210. Each channel 234 is sloped downwardly with respect to the longitudinal axis X by about 40°, and is dimensioned to receive a steel ball 236, as shown in FIG. 14. Thus, when the ocular treatment apparatus 210 is rotated through an angle of about 40° with respect to a horizontal axis, as shown in FIG. 13, the steel balls 236 slide through the channels 234 and strike a bottom surface in the eyecup 214, as will be described further below.

Figure 16:
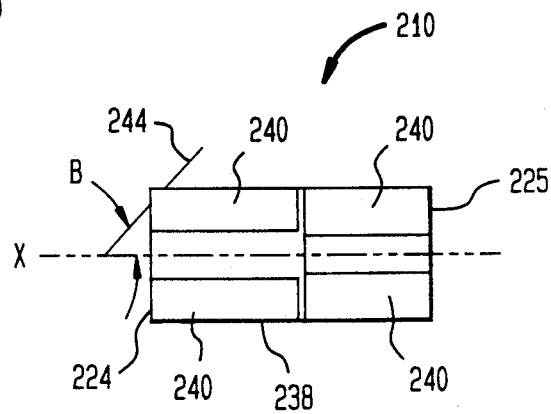
FIG. 16 is a side plan view of the inner casing of FIG. 14.

The inner casing 210 further defines an outer wall 238, shaped to slideably fit within the outer casing 216. The outer wall 238 defines four channels 240 extending along each of its four corners. The channels 240 are provided to facilitate the sliding movement of the outer casing 216 over the inner casing 210. The inner casing 210 further defines four finger slots 242 extending through the top wall 224. Each finger slot 242 is defined by an end wall 244. Each end wall 244 is sloped with respect to the longitudinal axis X of the inner casing 210 by an angle B, as shown in FIG. 16. The angle B is preferably about 45°.

In FIGS. 18 through 21, the eyecup 214 is illustrated in further detail. The eyecup 214 defines a peripheral edge 248 shaped to conformably engage the facial tissue covering the bone structure surrounding an eye. A dome-shaped wall 250 extends upwardly from the edge 248 to block the passage of light into a user's eye. The eyecup 214 further defines a substantially cylindrical opening 252 extending therethrough. The opening 252 is defined by a substantially cylindrical inner wall 254, concentric with the longitudinal axis X. A pair of substantially square notches 256 are formed within the cylindrical wall 254. The notches 256 are diametrically opposed to each other and extend along the cylindrical inner wall 254 in the axial direction X. The inner wall 254 and notches 256 are dimensioned to receive a locking member on the cover 220, as will be described further below.

A sighting opening 258 extends through the wall 250. The sighting opening 258 is positioned to permit light to pass therethrough. When the eyecup 214 is placed over an eye and the user looks at the opening 258, the eye is oriented upwardly. Thus, the medicament dispensed from the ocular vial 212 is permitted to fall into the exposed ocular cul-de-sac of the eye, as shown in FIG. 13.

Figure 21:
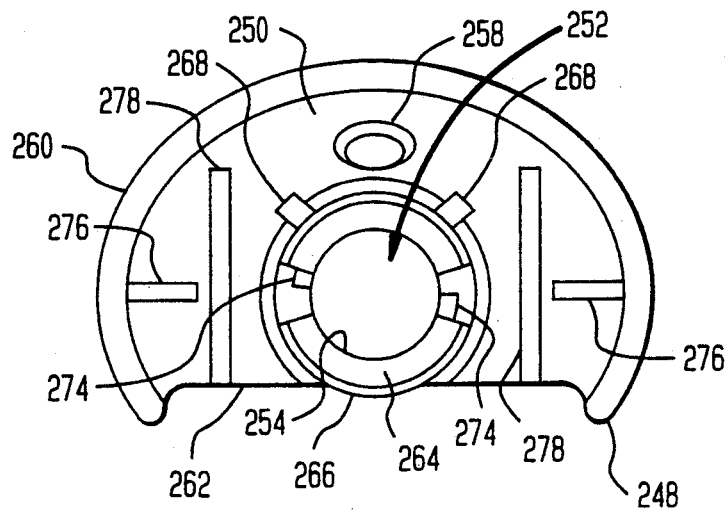
FIG. 21 is a top end plan view of the eyecup of FIG. 18.

The eyecup 214 further defines an outer wall 260 extending upwardly from the edge 248 and spaced apart from the dome-shaped wall 250, as shown in FIG. 21. A substantially flat indentation 262 is formed along one side of the wall 260. The indentation 262 is dimensioned to permit the eyelid depresser 218 to slide therethrough.

The eyecup 214 further defines a flange 264 extending upwardly from the dome-shaped wall 250, and surrounding the inner cylindrical wall 254. The flange 264 defines a substantially cylindrical outer wall 266. Two substantially square mounting tabs 268 project radially outward from the outer wall 266. The mounting tabs 268 are dimensioned to be received within two corresponding indentations 230 on the inner casing 210, to position the eyecup 214 with respect to the inner casing.

Figure 17:
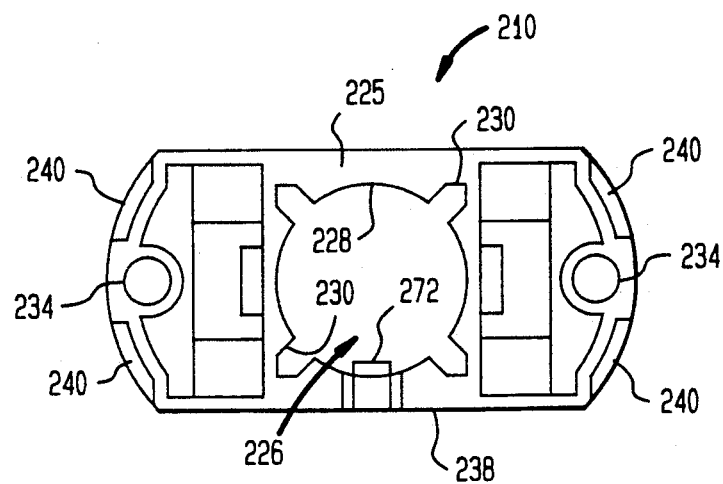
FIG. 17 is an enlarged, bottom end plan view of the inner casing of FIG. 14.
Figure 18:
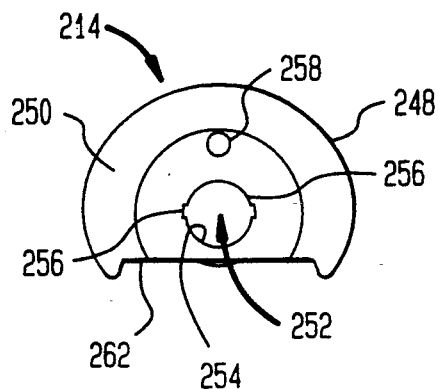
FIG. 18 is a bottom end plan view of the eyecup of the apparatus of FIG. 12.
Figure 19:
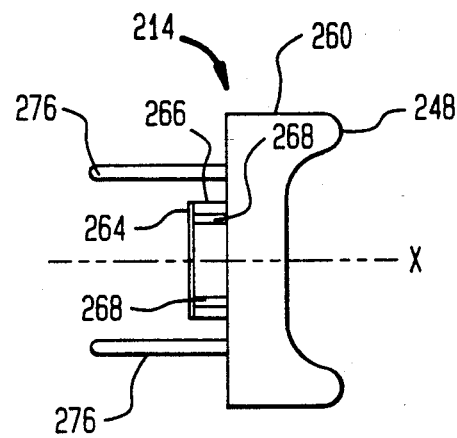
FIG. 19 is a top plan view of the eyecup of FIG. 18.
Figure 20:
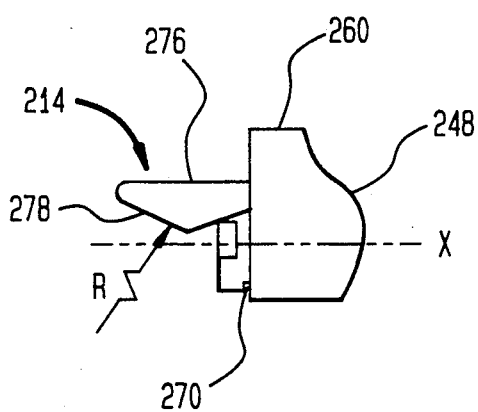
FIG. 20 is a partial cross-sectional, side plan view of the eyecup of FIG. 18.

A mounting notch 270 is formed within the base of the outer wall 266, as shown in FIG. 20, to mount the inner casing 210 to the eyecup 214. The inner casing 210 defines a chamfered tab 272 on the inside surface of its bottom end 225, which projects into the aperture 226, as shown in FIG. 17. The eyecup 214 is mounted to the inner casing 210 by inserting the flange 264 into the cylindrical wall 228, so that the mounting tabs 268 are inserted into the corresponding notches 230. The chamfered tab 272 is in turn pushed over the cylindrical wall 266 and snapped into the mounting notch 270, thus securing the eyecup 214 to the inner casing 210, as shown in FIG. 12.

The eyecup 214 further defines two bayonnet mounts 274 within the flange 264, as shown in FIG. 21. Each bayonnet mount 274 is located at the top end of a respective notch 256, to lock the cover 220 to the eyecup 214, as will be described further below. A pair of ribs 276 extend inwardly from the inside surface of the wall 260 on diametrically opposite sides of the flange 264. The ribs 276 are positioned so that when the eyecup 214 is mounted to the inner casing 210, each rib 276 is located immediately below a respective channel 234. Therefore, when the steel balls 236 slide through the channels 234, each ball strikes a respective rib 276. The steel balls 236 thus impart vibrations through the edge 248 of the eyecup into the facial tissue and bone structure surrounding the eye.

The eyecup 214 further defines a pair of depresser guides 278 projecting upwardly from the domed surface 250 on either side of the flange 264. As shown in FIG. 20, each depresser guide 276 defines a guide surface 278, which has a slight radius of curvature R. The radius of curvature R is dimensioned so that the guide surfaces 278 direct the eyelid depresser 218 downwardly toward the facial tissue below the eye, as will be described further below.

Figure 22:
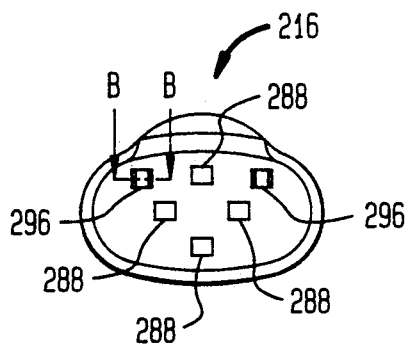
FIG. 22 is an enlarged, bottom end plan view of the outer casing of the apparatus of FIG. 12.
Figure 23:
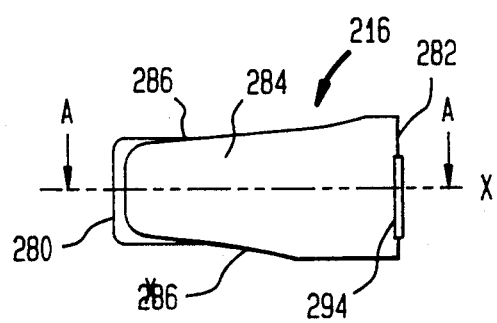
FIG. 23 is a side plan view of the outer casing of FIG. 22.

Turning to FIGS. 22 through 25, the outer casing 216 is shown in further detail. The outer casing 216 defines a closed end 280, an open end 282, and an outer wall 284. The outer wall 284 defines two gripping portions 286 located on opposite sides of the outer casing 216. Each gripping portion 286 slopes upwardly relative to the longitudinal axis X in the direction from the closed end 280 to the open end 282. As can be seen in FIG. 23, the gripping portions 286 provide a convenient surface for a user to grip the outer casing 216 and slide the outer casing relative to the inner casing 210, as will be described further below.

Figure 24:
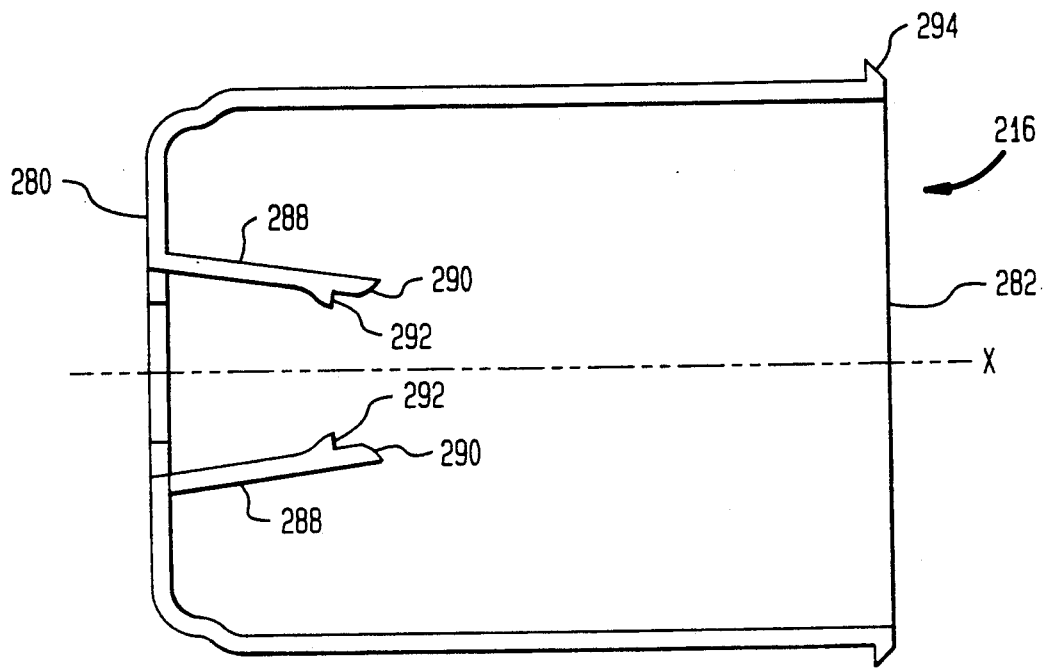
FIG. 24 is an enlarged cross-sectional view of the outer casing of FIG. 23, taken along the line A—A.
Figure 25:
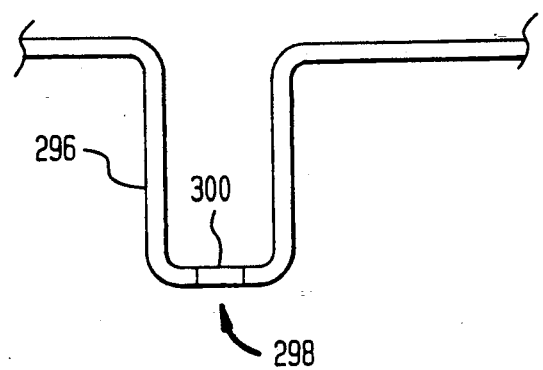
FIG. 25 is a magnified cross-sectional view of the depresser mount of the outer casing of FIG. 22, taken along the line B—B.

The outer casing 216 further comprises four fingers 288 projecting inwardly from the inside surface of the closed end 280, as shown in FIGS. 22 and 24. The four fingers 288 are equally spaced relative to each other about the longitudinal axis X of the apparatus. As shown in FIG. 24, each finger 288 defines a chamfered tip 290. A vial tab 292 is located immediately above each tip 290 and projects inwardly toward the longitudinal axis X. The vial tabs 292 are thus adapted to engage the ocular vial 212 by sliding the outer casing 216 toward the eyecup 214. The fingers 288 in turn depress the vial 212 to actuate the vial to release medicament, as will be described further below.

The outer casing 216 further defines a lip 294 extending along the outer surface of its open end 282. The lip 294 is dimensioned to snap into the tamper-resistant ring 222, as will be described further below. The outer casing 216 further comprises two depresser mounts 296 projecting inwardly from the inside surface of the closed end 280. A typical depresser mount 296 is illustrated in further detail in FIG. 25. Each depresser mount 296 defines an aperture 298 extending through the free end thereof, and a lip 300 extending around the aperture 298. The apertures 298 are dimensioned to receive the free ends of the eyelid depresser 218, to couple the eyelid depresser to the outer casing 216, as will be described further below.

Figure 26:
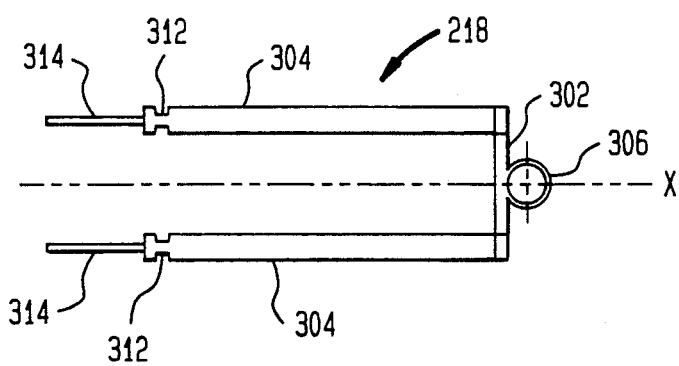
FIG. 26 is a top plan view of the eyelid depresser of the apparatus of FIG. 12.
Figure 27:
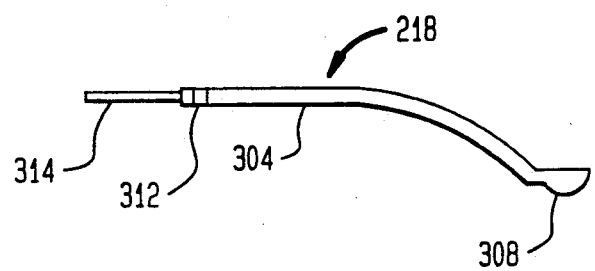
FIG. 27 is a side plan view of the eyelid depresser of FIG. 26.

Turning to FIGS. 26 and 27, the eyelid depresser 218 is shown in further detail. The eyelid depresser 218 comprises a crossbar 302 and two legs 304 projecting outwardly from either end of the crossbar 302. The two legs 304 extend in the axial direction X of the apparatus 200 in a parallel relationship to each other. As shown in FIG. 27, each leg 304 is curved downwardly toward the crossbar 302. Thus, when the eyelid depresser 218 is pushed by the outer casing 216, it is directed toward the facial tissue below the eye, as will be further described below.

A depresser tab 306 projects outwardly from the middle of the crossbar 302 in the opposite direction of the legs 304. The depresser tab 306 defines a substantially hemispherical outer surface 308, which is adapted to engage the facial tissue below an eye. The depresser tab 306 is made of a flexible polymeric material so that it can flex inwardly upon engaging the facial tissue below an eye, as shown in FIG. 13. A face cushion (not shown) made of a sponge-like polymeric material, can be placed over the depresser tab 306 to facilitate gently displacing the facial tissue below an eye.

Each leg 304 defines an indentation 312 adjacent to its free end. Each indentation 312 is dimensioned to receive therein a lip 300 of a respective depresser mount 296 on the outer casing 216. The eyelid depresser 218 further comprises a pair of guide strips 314, each strip projecting outwardly from the free end of a respective leg 304. The guide strips 314 are provided to guide the free ends of the legs 304 into the apertures 298 of the depresser mounts 296. The eyelid depresser 218 is coupled to the outer casing 216 by sliding the guide strips 314 into the respective apertures 298. The legs 304 are then pressed through the apertures 298, so that the lip 300 on each depresser mount 296 is secured within the respective indentation 312 of each leg 304, as shown in FIG. 13. Thus, the legs 304 are coupled to the depresser mounts 296 and slideably mounted through the rectangular apertures 232 and indentations 233 of the inner casing 210.

Figure 28:
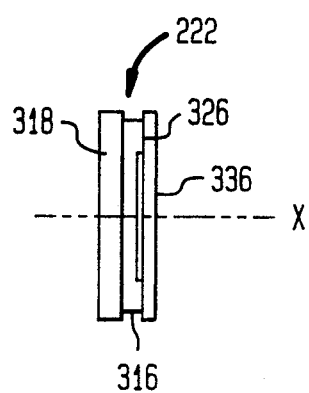
FIG. 28 is a side plan view of the tamper-resistant ring of the apparatus of FIG. 12.
Figure 29:
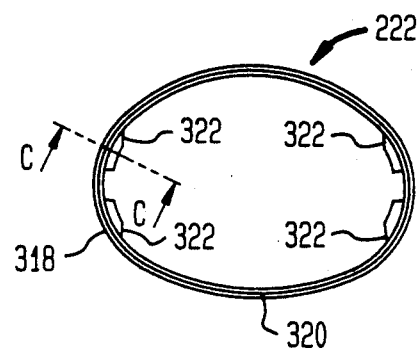
FIG. 29 is a top plan view of the tamper-resistant ring of FIG. 28.
Figure 30:
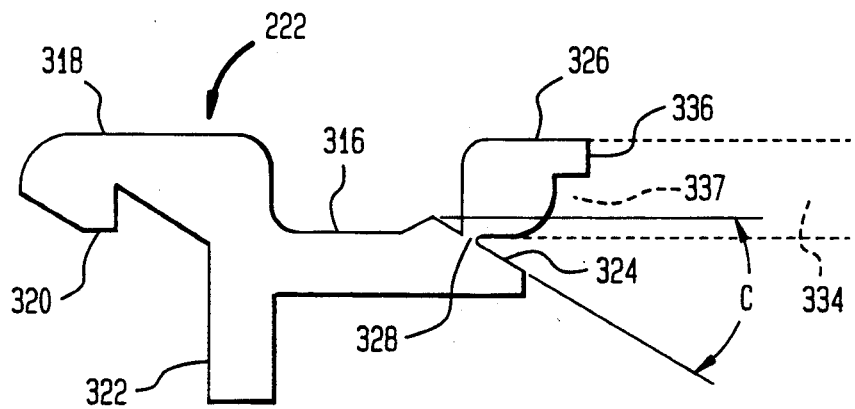
FIG. 30 is an enlarged, partial cross-sectional view of the tamper-resistant ring of FIG. 29, taken along the line C—C.

Turning to FIGS. 28 through 30, the tamper-resistant ring 222 is shown in further detail. The ring 222 comprises a bottom wall 316 shaped to correspond to the open end 282 of the outer casing 216. As shown in FIG. 30, a top wall 318 projects upwardly from the bottom wall 316 and defines a lip 320 projecting inwardly therefrom. The lip 320 is dimensioned to retain the lip 294 on the open end of the outer casing 216. Thus, the outer casing 216 is coupled to the tamper-resistant ring 222 by pressing its open end 282 into the ring 222, so that the lip 294 snaps into the space below the lip 320, as shown in FIG. 12.

The tamper-resistant ring 222 further comprises four tabs 322 spaced apart from each other and projecting inwardly from the bottom wall 316. The bottom wall 316 defines an outer surface 324, which is sloped inwardly by an angle C relative to the longitudinal axis X of the apparatus. The angle C is preferably about 30°. A cover ring 326 projects outwardly from the sloped surface 324, and is connected to the surface 324 by an annular breakable section 328. The breakable section 328 has a relatively slight cross-sectional thickness so that the cover ring 326 can be easily snapped away from the sloped surface 324, as will be described further below.

Figure 31:
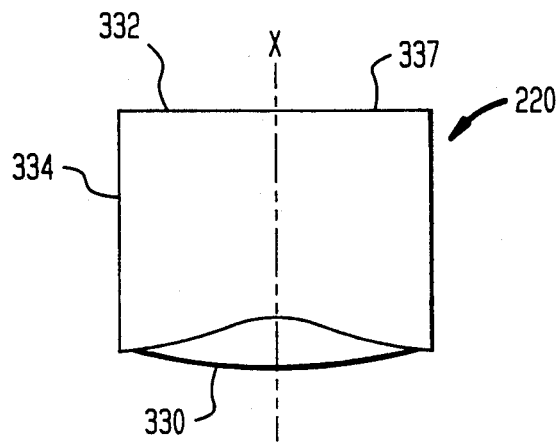
FIG. 31 is a top plan view of the cover of the apparatus of FIG. 12.
Figure 32:
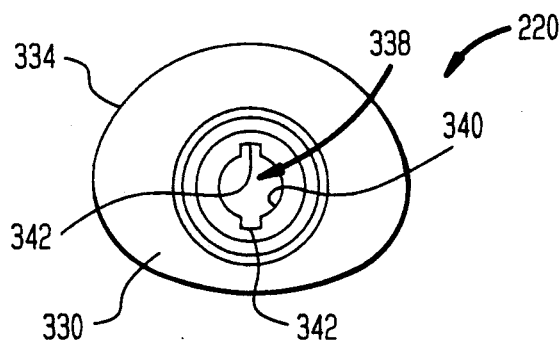
FIG. 32 is a bottom end plan view of the cover of FIG. 31.

Turning to FIGS. 31 and 32, the cover 220 is shown in further detail. The cover 220 defines a closed end 330, an open end 332, and an outer wall 334 extending therebetween. The outer wall 334 is shaped to fit over the outer wall 260 of the eyecup 214. As shown in FIG. 30, the cover ring 326 of the tamper-resistant ring 222 further defines a first welding lip 336, which is shaped to correspond to a second welding lip 337 formed on the open end 332 of the cover 220. The open end 332 of the cover 220 is fastened to the ring 222, as shown in FIGS. 12 and 30, in a manner known to those skilled in the art, such as by ultrasonic welding, or heat welding.

The cover 220 is welded to the tamper-resistant ring 222 after a vial 212 of medicament is inserted within the apparatus 200, and the apparatus is ready to be shipped by the manufacturer, such as a pharmaceutical company. The cover 220 cannot then be removed from the apparatus 200, unless the tamper-resistant ring 222 is fractured through the breakable section 328. The section 328 is fractured by holding the outer casing 216 and striking the bottom of the cover 220 against a firm surface. The open end 282 of the outer casing 216 is thus forced down against the four tabs 322. The force against the tabs 322 is transmitted by the sloped surface 324 against the cover ring 326 which, in turn, causes the breakable section 328 to fracture.

Figure 33:
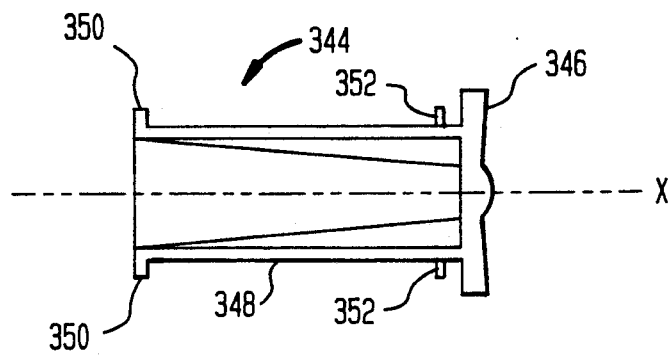
FIG. 33 is an enlarged cross-sectional view of the locking member for the cover of FIG. 32.

The cover 220 further includes an aperture 338 defined by a substantially cylindrical surface 340. The cylindrical surface 340 extends through the top wall 330 and is concentric with the longitudinal axis X. The cylindrical surface 340 defines therein a pair of notches 342 projecting radially outward from the axial center of the cover 220, and diametrically opposed to each other. The cylindrical surface 340 and notches 342 are dimensioned to receive a locking member, indicated generally as 344 in FIG. 33.

The locking member 344 comprises a flange 346 and a hollow stem 348 projecting outwardly therefrom. The stem 348 defines on the free end thereof a pair of mounting bayonnets 350. The bayonnets 350 are diametrically opposed to each other, and project outwardly in a direction substantially perpendicular to the longitudinal axis X. The bayonnets 350 are dimensioned to be received within the notches 256 and rotatably locked into the bayonnet mounts 274 of the eyecup 214.

A pair of mounting tabs 352 project outwardly from the stem 348, and are spaced immediately below the bottom surface of the flange 346. The tabs 352 are dimensioned to fit through the notches 342 in the top wall 330 of the cover 220. The locking member 344 is thus inserted through the aperture 338. The flange 346 is then rotated so that the tabs 352 prevent the locking member from being removed therefrom. As shown in FIG. 12, the free end of the stem 348 is positioned below the open end 330 of the cover 220. Therefore, if the cover 220 is removed from the apparatus 200 and accidentally dropped, the stem 330 will likely not contact the ground or other contaminated surfaces.

The cover 220 is locked to the eyecup 214 by sliding the bayonnets 350 through the notches 256 in the eyecup. Then, once the bayonnets are inserted into the bayonnet mounts 274, the flange 346 is rotated, so that the bayonnets 350 are locked into the bayonnet mounts 274. Therefore, once the locking member 344 is locked in place, a child has to simultaneously rotate the flange 346 and pull the cover away from the eyecup 214 to release the cover. As shown in FIG. 12, the locking member 348 is seated over the opening for the ocular vial 212 in the eyecup 214. Therefore, the locking member 348 and cover 220 prevent contaminating particles from contacting the ocular vial 212.

The ocular vial 212 is filled with medicament by a pharmaceutical company in a sterile environment. The ocular vial 212 is then covered with a cap 353, as shown in FIG. 12. Once the ocular vial 212 is covered with the cap 353, it can then be removed from the sterile environment without contaminating the medicament. The ocular vial 212 is then inserted into the inner casing 210.

The cap 353 is dimensioned to be pressed into the hollow stem 348, as shown in FIG. 12. Therefore, when the ocular vial 212 is inserted into the inner casing 210, the cap 353 is pressed into the stem 348, as shown in FIG. 12. Then, when the cover 220 is removed by the user, the cap 353 is removed with the cover inside the stem 348.

Figure 34:
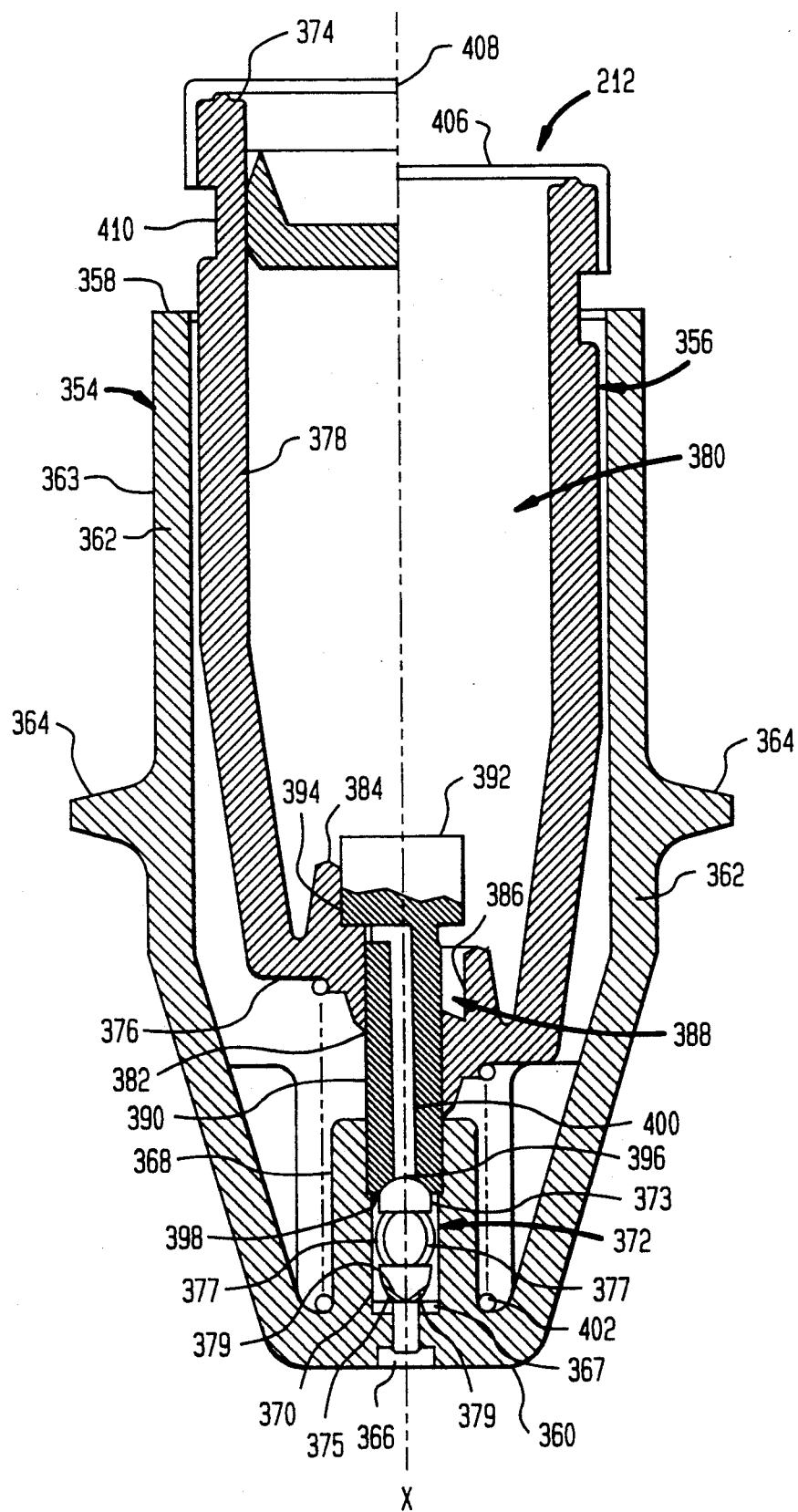
FIG. 34 is an enlarged cross-sectional view of the ocular vial of the apparatus of FIG. 12, illustrating on the left side the position of the ocular vial when medicament is released therefrom, and illustrating on the right side the position of the ocular vial when actuated to release medicament.

Turning to FIG. 34, the ocular vial 212 is shown in further detail. The ocular vial 212 comprises a rigid outer body 354 and a rigid inner body 356 slideably mounted within the outer body 354. The outer body 354 defines an open end 358, a closed end 360, and an outer wall 362 extending therebetween. The outer wall 362 defines a substantially cylindrical surface 363 dimensioned to be received within the cylindrical wall 228 of the inner casing 210. A pair of mounting nubs 364 project outwardly from the cylindrical surface 363 in a direction substantially perpendicular to the longitudinal axis X. The mounting nubs 364 are diametrically opposed to each other and dimensioned to fit within two corresponding indentations 230 in the inner casing 210.

The ocular vial 212 is thus mounted within the inner casing 210 by inserting the closed end 360 into the aperture 226 and cylindrical wall 228. The ocular vial 212 is positioned within the cylindrical wall 228, so that the mounting nubs 364 are inserted within the corresponding indentations 230. The ocular vial 212 is then pushed inwardly until its closed end 360 is seated against the flange 264 of the eyecup 214. As shown in FIG. 12, because the closed end 360 of the ocular vial 212 is located within the eyecup 214, it is protected from contact with contaminated surfaces.

The outer body 354 of the ocular vial 212 further defines a nozzle orifice 366 extending through the closed end 360 concentric with the longitudinal axis X. A first valve seat 367 extends around the nozzle orifice 366 on the inside surface of the closed end 360. A cylindrical wall 368 projects upwardly from the inside surface of the closed end 360, and defines a valve chamber 370 extending therethrough. The valve chamber 370 is oriented along the longitudinal axis X and is in fluid communication with the nozzle orifice 366.

A valve 372 is seated within the valve chamber 370. The valve 372 includes a top lobe 373, a bottom lobe 375, and two flexible members 377 extending therebetween. The valve 372 further defines several grooves 379 extending along the outer surface of the bottom lobe 375. The bottom lobe 375 is dimensioned to be seated within the first valve seat 367 to cover the nozzle orifice 366. The grooves 379 are in turn provided to allow medicament to flow therethrough and thus through the nozzle orifice 366 for release into an eye, as will be described further below.

The inner body 356 defines an open end 374, a closed end 376, and an outer wall 378 extending therebetween. The outer wall 378 is dimensioned to be slideably received within the outer wall 363 of the outer body 354, as shown in FIG. 34. The outer wall 378 thus defines a reservoir 380 for holding medicament. The inner body 356 further defines an orifice 382 extending through the closed end 376, concentric with the longitudinal axis X. A flange 384 projects upwardly from the closed end 376 and surrounds the orifice 382. The flange 384 defines a cylindrical surface 386 spaced away from, and extending around the orifice 382, thus defining a drop cavity 388 therein.

The ocular vial 212 further comprises a shaft 390 defining a cylindrical head 392 on one end thereof. The other end of the shaft 390 is inserted through the orifice 382, and threadedly engaged within the free end of the cylindrical wall 368 of the outer body 354. Thus, the inner body 356 can slide within the outer body 354 along the shaft 390, between the head 392 and the free end of the cylindrical wall 368.

The shaft 390 further defines a first orifice 394 extending through a side wall thereof immediately below the head 392. A second orifice 396 extends through the free end of the shaft 390, concentric with the longitudinal axis X. The free end of the shaft 390 further defines a second valve seat 398 surrounding the second orifice 396. The second valve seat 398 is shaped to seat the top lobe 373 of the valve 372. The shaft 390 further defines a channel 400 extending between the first orifice 394 and the second orifice 396, to permit medicament to flow therethrough.

The ocular vial 212 further comprises a coil spring 402, illustrated schematically. The coil spring 402 is seated between the closed end 376 of the inner body 356, and the inside surface of the closed end 360 of the outer body 354. Thus, the inner body 354 is normally spring biased against the head 392, as shown on the left side of FIG. 34.

The ocular vial 212 further comprises a cap 404 inserted into the open end 374 of the inner body 356. The cap 404 is shaped so that the medicament within the chamber 380 does not leak between the cap and the outer wall 378. When medicament is dispensed from the chamber 380, the cap 404 slides downwardly under the suction forces within the chamber 380, and is thus maintained in close proximity with the medicament.

The ocular vial 212 further comprises a lid 406 mounted over the open end 374 of the inner body 356. The lid 406 defines an aperture 408 extending through a top wall thereof. The aperture 408 is provided to permit airflow therethrough when the cap 404 slides downwardly under the suction forces within the chamber 380. The lid 406 is dimensioned so that its top edge abuts against the vial tabs 292 on the fingers 288 of the outer casing 216. The vial tabs 292 are thus used to push the inner body 356 inwardly to actuate the vial 212, as will be described below. The inner body 356 further defines a notch 410 within the outside surface of the outer wall 378. The notch 410 is located immediately below the cap 406 and extends along the periphery of the outer wall 378. The notch 410 is provided to allow air to pass therethrough when depressing the inner body 356 within the outer body 354.

The ocular vial 212 is actuated to release medicament by pushing the inner body 356 toward the outer body 354, against the spring 402, as shown on the right side of FIG. 34. Medicament in the reservoir 380 is then permitted to flow into the drop cavity 388 and in turn into the channel 400. When the pressure is released from the inner body 356, the spring 402 pushes the inner body 356 upwardly into its initial position, as shown on the left side of FIG. 34. The cylindrical surface 386 is thus pushed over the head 392, so that the medicament within the drop cavity 388 is pressurized and thus forced through the first orifice 394 and into the channel 400.

The pressurized medicament in the channel 400 flows into the second orifice 396 and over the top lobe 373 of the valve 372. The pressure of the medicament causes the flexible members 377 to flex outwardly, as shown in FIG. 34, so that the top lobe 373 moves down and away from the second orifice 396. As a result, the pressurized medicament is permitted to flow into the valve chamber 370. The pressurized medicament in turn flows through the grooves 379 in the bottom lobe 375 and into the nozzle orifice 366. Thus, a pressurized discharge of medicament is released through the nozzle orifice 366 and into the everted cul-de-sac. The pressurized discharge is particularly suitable for use in low gravity environments, where gravity cannot be used to cause a drop of medicament to fall into the eye.

The drop cavity 388 is dimensioned so that an exact amount of medicament is released each time the ocular vial 212 is actuated. Once the pressurized medicament is released, the top lobe 373 is moved upwardly by the flexible members 377 and into the second valve seat 398. The valve 372 thus prevents air or other impurities from entering the channel 400 that might contaminate the medicament in the chamber 380.

It should be noted that other types of ocular vials can equally be used with the apparatus of the present invention. For example, the ocular vials shown and described in co-pending U.S. patent application Ser. No. 07/322,761, filed Mar. 13, 1989, which is expressly hereby incorporated by reference as part of the present disclosure, could be used with the apparatus of the present invention. The modifications necessary for the ocular vials shown in U.S. application Ser. No. 07/322,761 or to the apparatus of the present invention, necessary for these apparatus to be used with each other, are within the knowledge of those skilled in the art.

In the operation of the apparatus 200, a user removes the cover 220 and places the edge 248 of the eyecup 214 on the facial tissue surrounding the eye, as shown in FIG. 13. The user then tilts his or her head back, and rotates the apparatus 200 upwardly over the eye, while simultaneously looking toward the sighting opening 258. Then, when the user feels the vibrations of the steel balls 236 striking the eyecup 214, the apparatus 200 is properly positioned to release medicament into the eye.

The medicament within the vial 212 is released by pushing the outer casing 216 over the inner casing 210. The sliding movement of the outer casing 216 simultaneously pushes the eyelid depresser 21 through the apertures 232 and indentations 233 in the inner casing 210. The eyelid depresser 218 is in turn deflected downwardly over the guide surfaces 278 of the depresser guides 276. The depresser tab 308 thus gently engages the facial tissue below the eye, and in turn displaces the facial tissue downwardly, as the outer casing 216 is further depressed. The displaced facial tissue in turn displaces the lower eyelid, so as to expose the ocular cul-de-sac to receive a drop of medicament, as shown in FIG. 13.

When the outer casing 216 is pushed over the inner casing 210, the fingers 288 engage the lid 406 on the ocular vial 212. The tips 290 of the fingers are forced over the edge of the lid 406. Then, as the outer casing 216 is pushed further down, the vial tabs 292 engage the lid 406 and, in turn, push the inner body 356 toward the outer body 354. Then, about when the inner body 356 is fully depressed, as shown on the right side of FIG. 34, the tips 290 of the fingers 288 engage the sloped surfaces 244 on the inner casing 210.

The tips 290 are then forced outwardly along the sloped surfaces 244. The vial tabs 292 are therefore also forced outwardly away from the lid 406 of the ocular vial 212. Then, once the vial tabs 292 are spread away from the lid 406, the spring 402 drives the inner body 356 upwardly, as shown on the left side of FIG. 34. The medicament is then released through the orifice 366, into the exposed ocular cul-de-sac of the eye.

One advantage of the present invention, is that by displacing the lower eyelid and exposing the ocular cul-de-sac, the medicament is released onto the exposed cul-de-sac and, as a result, the effectiveness of the medicament is maximized. The ocular cul-de-sac is both a relatively low sensitivity area, and a low tear turnover area of the eye. The eye normally blinks with the upper eyelid to place tears over the cornea. Therefore, by placing medicament in the ocular cul-de-sac, a blinking reaction by the patient is minimized. However, if the patient does blink, the blinking likely will not substantially displace the medicament beneath the lower eyelid. Therefore, by employing the apparatus of the present invention, the medicament is not easily diluted and its residence time within the eye is increased so as to maximize its effectiveness.

After the medicament is released into the eye, the user removes the apparatus 200 away from the eye. When the apparatus 200 is moved away from the eye, the spring 217 pushes the outer casing 216 away from the inner casing 210, back into its initial position, as shown in FIG. 12. The outer casing 216 simultaneously carries the eyelid depresser 218 back through the inner casing 210. The apparatus 200 can then be used to release another drop of medicament, in the same way as described above.

What is claimed is:

1. An apparatus for applying medicament to an eye, comprising:
   a housing for receiving medicament for an eye and including a surface shaped to engage the facial tissue adjacent to an eye;
   an eyelid displacing member supported from the housing and moveable to engage the facial tissue and lower the eyelid to expose the ocular cul-de-sac; and
   a dispensing unit for dispensing medicament received within the housing upon the eyelid displacing member engaging the facial tissue and lowering the eyelid to release the medicament into the exposed ocular cul-de-sac.

2. An apparatus as defined in claim 1, wherein the housing includes
   a first housing member for receiving the dispensing unit; and
   a second housing member moveable relative to the first housing member and coupled to the displacing member, the displacing member thus being adapted to engage the facial tissue and lower the eyelid by moving the second housing member relative to the first housing member.

3. An apparatus as defined in claim 1, wherein the dispensing unit includes a medicament container supported within the housing for holding medicament and releasing medicament in response to the movement of the displacing member engaging the facial tissue to lower the eyelid.

4. An apparatus as defined in claim 1, further comprising means for directing a user's cornea upwardly to facilitate exposure of the ocular cul-de-sac.

5. An apparatus as defined in claim 4, wherein the means for directing includes a sighting opening within the housing for directing the user's eye to look through the sighting opening and facilitate exposure of the ocular cul-de-sac.

* * * * *